US011439322B2

(12) United States Patent
Garay (10) Patent No.: US 11,439,322 B2
(45) Date of Patent: Sep. 13, 2022

(54) METHOD AND APPARATUS FOR SPORTS AND MUSCLE MEMORY TRAINING AND TRACKING

(71) Applicant: Peter Garay, San Leandro, CA (US)

(72) Inventor: Peter Garay, San Leandro, CA (US)

( * ) Notice: Subject to any disclaimer, the term of this patent is extended or adjusted under 35 U.S.C. 154(b) by 116 days.

(21) Appl. No.: 16/704,960

(22) Filed: Dec. 5, 2019

(65) Prior Publication Data

US 2021/0169372 A1    Jun. 10, 2021

(51) Int. Cl.
*A61B 5/021* (2006.01)
*A61B 5/11* (2006.01)
*A61B 5/00* (2006.01)
*G09B 19/00* (2006.01)
*A63B 71/06* (2006.01)

(52) U.S. Cl.
CPC ............... *A61B 5/11* (2013.01); *A61B 5/486* (2013.01); *A61B 5/681* (2013.01); *A61B 5/7415* (2013.01); *A61B 5/7455* (2013.01); *A63B 71/0622* (2013.01); *G09B 19/0038* (2013.01); *A61B 5/6829* (2013.01); *A61B 5/6895* (2013.01); *A61B 2562/0219* (2013.01); *A63B 2071/0625* (2013.01); *A63B 2071/0655* (2013.01); *A63B 2220/40* (2013.01); *A63B 2220/806* (2013.01); *A63B 2220/833* (2013.01); *A63B 2220/836* (2013.01); *A63B 2225/50* (2013.01)

(58) Field of Classification Search
None
See application file for complete search history.

(56) References Cited

U.S. PATENT DOCUMENTS

| | | | | |
|---|---|---|---|---|
| 7,602,301 B1* | 10/2009 | Stirling | ............... | G06K 9/00 340/573.7 |
| 7,771,320 B2* | 8/2010 | Riley | ............... | G16Z 99/00 434/238 |
| 9,642,415 B2* | 5/2017 | Pease | ............... | A61B 5/1118 |
| 9,679,494 B2* | 6/2017 | Ellis | ............... | G06F 3/16 |
| 10,019,806 B2* | 7/2018 | Perry | ............... | G06T 7/292 |
| 10,039,969 B2* | 8/2018 | Burton | ............... | G06V 40/23 |
| 10,467,926 B2* | 11/2019 | Ghaffari | ............... | H04W 4/38 |
| 10,789,708 B1* | 9/2020 | Chuang | ............... | A63B 1/00 |
| 2006/0204045 A1* | 9/2006 | Antonucci | ............... | G06T 11/206 382/103 |
| 2009/0076765 A1* | 3/2009 | Kulach | ............... | A61B 5/6807 702/141 |
| 2010/0201512 A1* | 8/2010 | Stirling | ............... | A61B 5/1127 340/539.11 |
| 2012/0015778 A1* | 1/2012 | Lee | ............... | A63B 71/0686 482/8 |

(Continued)

*Primary Examiner* — Sunit Pandya (57) ABSTRACT

An accelerometer is mounted on a location of a user's body, sports equipment, or other device and tracks movement. Data describing the user's movement(s) may be saved or uploaded for distribution. The user's movement(s) may be compared to previously saved or downloaded movement data and an audio, vibrational, electrical, or other alert may be activated when the movement data is outside a predetermined range from the previously saved, pre-programmed, or downloaded movement. The invention is useful at least in various forms of physical therapy, sports training, and job training, and provides synergy when utilized in conjunction with other motion help related devices.

12 Claims, 8 Drawing Sheets

(56) References Cited

U.S. PATENT DOCUMENTS

| | | | |
|---|---|---|---|
| 2012/0078396 A1* | 3/2012 | Case, Jr. ............ | A63B 24/0003 |
| | | | 700/91 |
| 2012/0283855 A1* | 11/2012 | Hoffman ................ | G16Z 99/00 |
| | | | 700/91 |
| 2017/0151463 A1* | 6/2017 | Barfred .............. | G09B 19/0038 |

* cited by examiner

METHOD AND APPARATUS FOR SPORTS AND MUSCLE MEMORY TRAINING AND TRACKING

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Field of Invention

The present invention relates to training and physical therapy and particularly to movement and training muscles to follow exemplary paths such as those prescribed by a physician/therapist, a desired path of motion in a sporting activity, or other uses where tracking and/or feedback or muscle or other motion can be used advantageously.

Description of Related Art

Currently many devices are available for viewing and commenting on motions. For example, video is commonly used in physical therapy to instruct patients how to perform particular motions having benefit for the patient's recovery. Sports players often review tapes or video to analyze and improve motion such as their form when kicking a football or pitching in baseball.

SUMMARY OF THE INVENTION

The present inventor has realized the need for improved tracking of motion and feedback to a patient or sports player. In one embodiment, the present invention provides a wearable device that detects motion data and provides feedback according to a comparison or other analysis.

The present invention realizes that simplicity in operation is a valuable commodity, and, in an efficient form, the invention comprises an electronic device with accelerometers that detect motion and provide direct and immediate feedback to a user. Such feedback is, for example, through audio (e.g., high/low left/right, etc.).

The MMD is a preferably arranged so as to be pocket sized or watch sized (or smaller), and is a device that can record its motion and then use the recorded motion to provide feedback to a user. The MMD uses a gyroscope to measure angular velocity about 3 axes: x, y, z. With this, the object's orientation (equipment, user's hand, foot, etc.) in 3D space. An accelerometer measures acceleration (a change of velocity) across single axis. Multiple accelerometers may be utilized. A magnetometer may be used to detect the Earth's magnetic field, to determine motion, orientation and heading. In conjunction with the accelerometer(s) and gyroscope, an absolute heading of the device may be determined.

In one embodiment, a power button initiates the device, powering it up ready. A selector switch is set to a position for recording, and the MMD is ready to record the user's motion, saving it in memory. Upon setting the switch to a play position, the device will stop recording user's movement and is ready to analyze the user's motion compared to the recording.

The invention includes removing irrelevant motion data before the start of the move and after the move, but in some embodiments, keeping enough data before the motion if it is relevant for use in embodiments that pre-identify a motion the user may be about to perform.

In analyze mode, the user performs a motion. If the results match (the user's motion matches the recording), the device produces, for example, a distinguishable beeping sound (or a chime, or no sound at all). If the results don't match, the device produces different beeping sounds. Non matching sounds or alerts/alarms may be more pressing in nature, encouraging the user to do something different. In one embodiment, the sounds are coaching voices, such as instructions to "pull up," "lower," etc. The sounds are produced in real time, so during, or at least right after each movement execution, the user gets instant feedback to know whether the move execution was successful or not.

With wireless capability (e.g., Bluetooth), the MMD can be connected to a smartphone, server, the Internet, or other devices (including other MMDs). When connected to a smartphone, data recorded by the MMD (e.g., all data or move/motion specific data) can be stored in the phone. Individual moves or motions may be stored on the smart phone and may be uploaded to the MMD's memory. The smart phone may provide a platform for an application to facilitate the above, select moves and/or motions, and to identify tweaks that may be desired to the various moves (e.g., faster, slower, varying force, etc.).

With the use of the app, the users can store multiple recorded movements and select among the recorded movements and/or downloaded movements.

With the flicker (switch) in its right (or play) position, the users can then decide which movement they want to practice (recreate). With the flicker in its left (or record) position, the users can record more movements. The smartphone connection is optional and not necessary for the use of the device. The user may select from multiple stored movements without a smartphone app by, for example, moving the selector switch back and forth 3 times to select the $3^{rd}$ recorded movement. In one embodiment, an additional switch with multiple positions is added to select the potentially multiple recorded movements.

Figure 4:
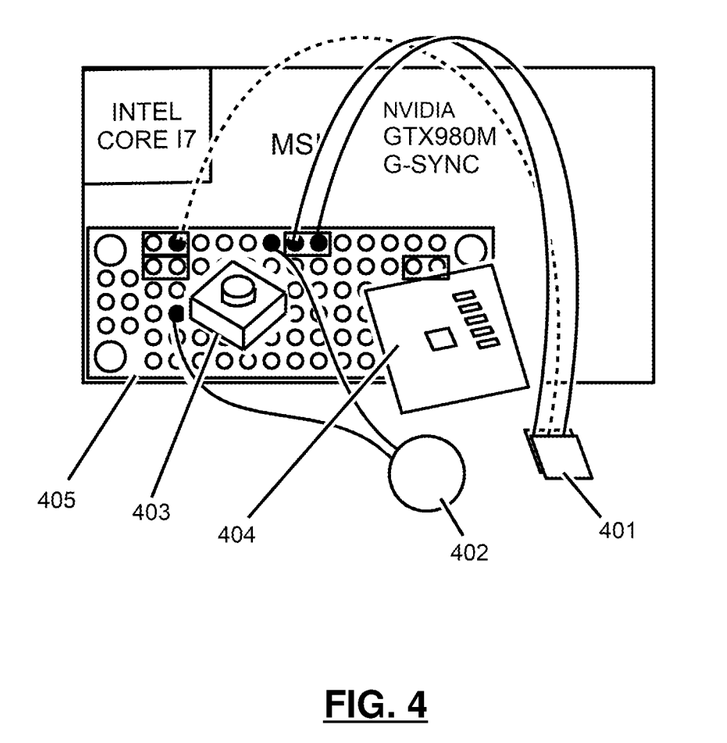
FIG. 4 is a photograph of prototype electronics configured to implement an MMD according to an embodiment of the present invention.

In yet another embodiment, the functions of the switch selector 401 and power button are combined into a single button. For example, the MMD can be powered-up by pressing the button, and powered-down by pressing the button for a predetermined length of time (e.g., 3-seconds or longer). Changing between modes may be performed by holding the button down for another pre-determined length of time (e.g., 2-seconds to change modes—e.g., switch between record and play modes). If the MMD holds multiple programs, the programs may be cycled by yet another duration press (e.g., a momentary press changes programs—e.g., momentary press switches between recorded program 1 (forehand), recorded program 2 (backhand), and possibly others). In one embodiment, the MMD signals the program change by a beep or series of beeps (e.g., 1-beep for program 1, 2 for program 2, etc.).

Pre-recorded moves (e.g., from professional table tennis players, tennis players, and other movements that require professional players to do perform them) can be downloaded with the use of the app. Programming and physical and/or wireless connections to the MMD may also provide a direct way to download movements that may be, for example, selected using a website and then automatically downloaded to the MMD.

The MMD can record statistics of a user's movements, and users can upload their statistics and their own movements online, or share them via social media. With all the data stored for any given movement, the move can be displayed on the smartphone's screen visually so that the user can evaluate/visualize the move, see how the MMD was moving in space, etc.

The MMD is not only useful for specific sports. It can be used for any desired movement—sport, muscle training, physical therapy, etc. In one embodiment, a physical therapist, doctor, or coach can directly upload motions into a patient or athlete's MMD, and a professional's app or computer program can maintain a set of preferred or prescriptible (prescribed motion) motions and allow the professional to enter an alert, notification, text, or email with any explanation or notes the professional may want to convey to the user. The present invention includes automatically entering a billing line into a patient or athlete's account for uploading the motion and any review, discussion, or analysis performed by the professional.

It can aid for training of table tennis serves, kicking soccer ball in a specific user determined way, aid in walking in a specific user determined way, help with various user determined muscle movement training. All movements are performed by the user and the device does not claim to help with healing injuries, nor is it responsible for improper use. However, if certain motions are helpful in the healing process, such as those prescribed by a physician or physical therapist, the motions will have benefit.

The user may determine exactly what kind of movement he wishes to execute, and the device aids the user to perform the specific move into perfection by repeatedly practicing it. Just like when we walk, we don't intuitively think "I'm going to lift my right leg up, then move it forward, then put it down and repeat the same with my left leg". We do the moves subconsciously, where our muscles are trained to do moves without the "how to do them thinking". Repeated use of the MMD helps move that process along for any recorded motion.

In different embodiments, the MMD can help with performing very specific moves in a way that helps with muscle regeneration after injuries. Various movements are done for physical therapy. If recorded correctly, then the user can use the MMD to execute those movements with instantaneous feedback. This can serve as an additional help with physical therapy (or muscle strengthening—to avoid medicinal use).

In another embodiment, the present invention provides a method of analyzing motion comparted to a desire range of motion. The present invention includes an application on a phone, computer, or other electronic device that receives motion data, compares it to a baseline, and sends feedback signals in real or near real-time such that a user knows immediately if the motion is correct or off-track. The feedback may include an audible alarm, vibration, electrical signal, etc.

The present invention includes multiple types and instances of feedback for the adjustment or correction of motion. For example, in one embodiment the present invention retrieves stored and/or real-time data and displays caricatures or images on a smartphone performing a motion performed by a user along with indicia of differences between the motion and a desired motion. The differences indicia include, for example, highlighted body parts or portions of body parts outside acceptable limits of the motion as the caricature or image performs the motion (e.g., playback of the user's motion with indicia added).

The indicia may include motion streaks, arrows, that help suggest the desired motion. Such streaks or arrows may, for example, be placed at critical junctures before the incorrect motion occurs which preconditions the reviewing user before viewing the highlighted incorrect motions. Advantageously, the differences indicia may correspond directly to audio or vibrational feedback the user received while performing the motion. Such review provides double cues that reinforce the proper motion. In yet another embodiment, the vibrational or audio feedback is repeated while reviewing a caricature or image playback (with or without visual indicia of errors or correct motion) so as to provide yet another correlation to the proper motion and adjustment required to perform it properly.

In one embodiment, the feedback is primarily audio having a sound that is related to the motion being performed. The present invention includes methods for identifying moves and comparing motion to motions stored in a database, and others.

Portions of both the devices and methods may be conveniently implemented in programming on a general purpose computer, or networked computers, and the results may be displayed on an output device connected to any of the general purpose, networked computers, or transmitted to a remote device for output or display. In addition, any components of the present invention represented in a computer program, data sequences, and/or control signals may be embodied as an electronic signal broadcast (or transmitted) at any frequency in any medium including, but not limited to, wireless broadcasts, and transmissions over copper wire(s), fiber optic cable(s), and co-ax cable(s), etc.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
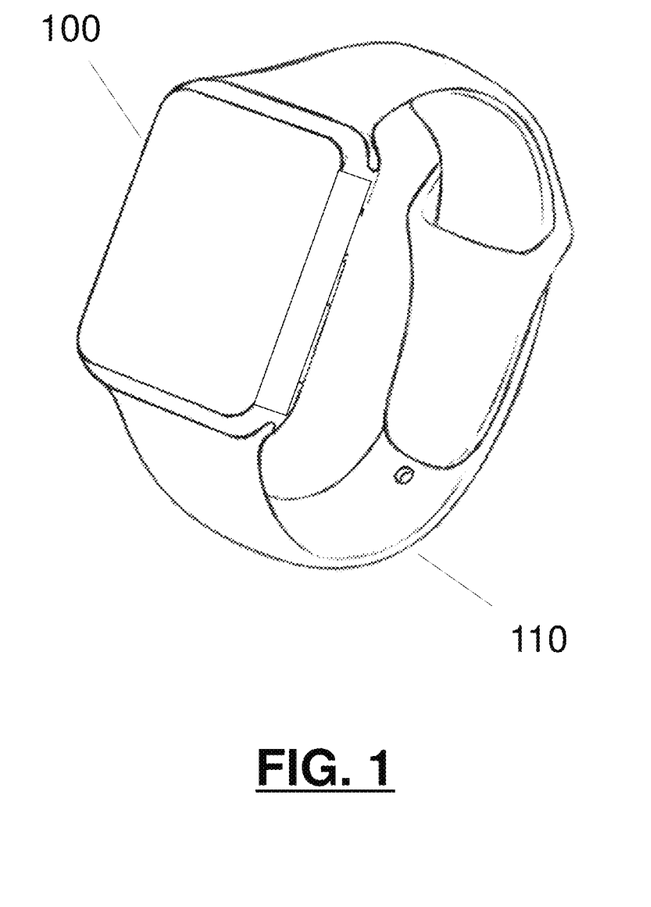
FIG. 1 is drawing illustrating a band having an attached Muscle Memory Device (MMD) according to an embodiment of the present invention.

Referring now to the drawings, wherein like reference numerals designate identical or corresponding parts, and more particularly to FIG. 1 thereof, there is illustrated a Muscle Memory Device (MMD) 100 according to an embodiment of the present invention. The tracking sensor is attached to a band 110 which may be affixed to a wrist, foot, or other appendage of a patient or sports trainee. In another embodiment, the MMD 100 may include adhesive for attachment directly to the skin at various locations of the user.

The MMD 100 may be configured to operate in different ways. In one embodiment, the MMD 100 operates as a motion tracking and alert system. For example, the MMD 100 is programmed to recognize physical therapy movements and alert the user at predetermined points in the movement. Such alerts occur, for example, when the user moves outside a range of motion deemed appropriate for the therapy maneuver being performed. The alerts are, for example, real-time alerts notifying the user the moment the user's range of motion deviates sufficiently to be incorrect.

For example, a user is prescribed a movement such as a rotating leg lift (e.g., lifting leg with a small amount of clockwise then counter-clockwise rotation). If the user fails to lift the leg high enough, an alert or alarm sounds. Similarly, if the user fails to rotate along with or during the lift, an alert or alarm sounds. As will be discussed in more detail further below, the same type of alert or alarm may be implemented in other areas, such as sport moves, part of sporting equipment, practice in professional moves in many different fields, etc. The alert or alarm may be initiated based on other than improper moves, such as a reward for extra extension other than that prescribed if deemed appropriate (e.g., additional extension in some cases might not be desirable).

Figure 2:
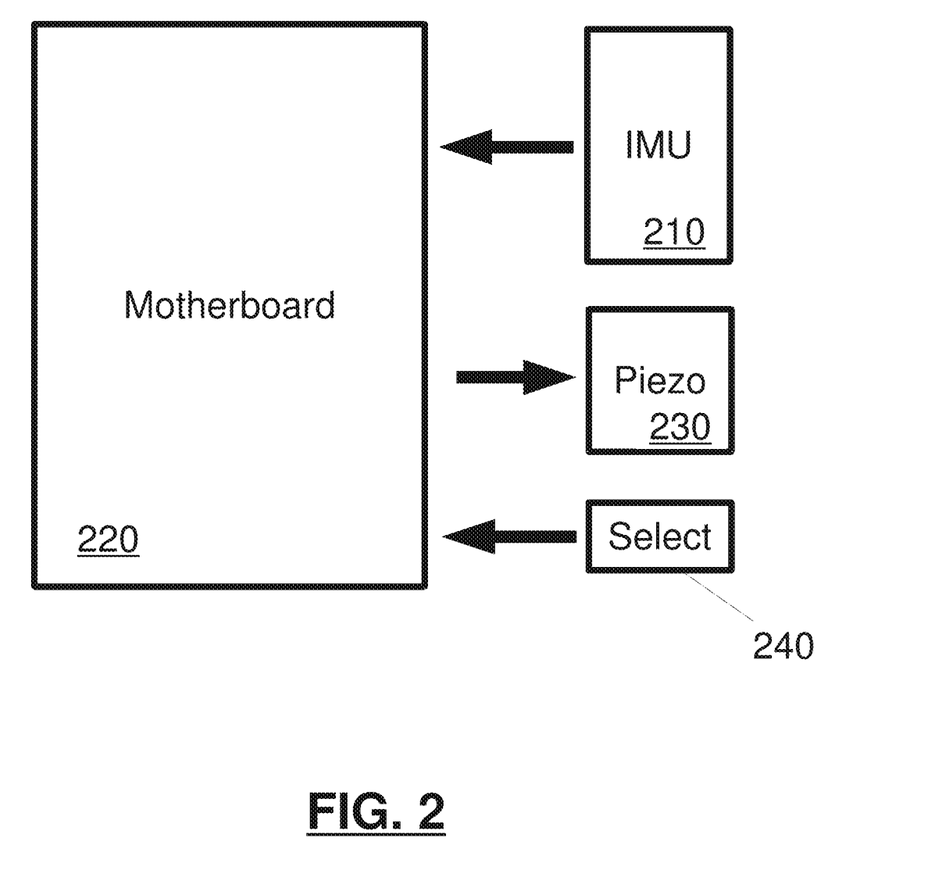
FIG. 2 is a block diagram illustrating components and communications according to an embodiment of the present invention.

FIG. 2 is a block diagram 200 illustrating components and communications according to an embodiment of the present invention. An IMU 210, which, for example, is embedded in the MMD 100, senses motion in various axes, and provides the motion data to a motherboard having a central processing unit and programming to implement the present invention. [A compass, GPS, or other device for direction finding may also be included.] The programming may include, for example, data storage of inertial measurements, averages, or samples from one or more of a variety of physical therapy or sports motions (actual moves or training exercises, for example) and routines that compare a user's motion to a stored motion.

For example, in one embodiment a stored motion may be stored based on position, velocity, and acceleration over a predetermined number of samples per second. A pattern of samples is matched with real-time data from the IMU 210, where the comparison is immediate and a decision is made whether the user's current motion is correct or deviating from a corresponding sample or samples. When deviating the alert/alarm is sounded (e.g., piezo 230), notifying the user to correct or improve the motion. Upon sufficient correction, the alert/alarm is silenced.

In one embodiment, the alarm is customized based on the motion. For example, the alarm may give a cue as to the appropriate motion or corrective action needed. In the case of an audio alarm, if the user's motion is from a high position to a low position, and the stored movement is from a low position to a high position (or if just generally, the user's motion needs to be more up than down) the alarm may be a tone that varies from low to high—an audio cue as to how the motion should proceed.

The MMD 100 may include a select switch 240 that inverts moves by switching between a left-handed (or left-sided) motion to a right-handed (or right-sided) motion. Changing from a left to right-sided (or visa-versa) motion may be performed via a mathematical translation of the stored move from a first-side perspective to a second-side perspective. In one embodiment stored moves may be adjusted for an individual user's particular circumstances. For example, in the case of a patient or trainee with a prosthetic limb, the stored data may account for non-standard movements made because of the prosthetic. Adjustments may also be made to account for varying user sizes (taller, shorter longer, heavier, etc.) Accordingly, the present invention includes a mechanism to adjust moves (e.g., professional moves downloaded from the Internet) such that they fit physical characteristics of an individual user.

More than one motion or move may be stored in the MMD, and a select switch 240 may be configured to select different moves or measurements from different positions (e.g., wrist or ankle). The select switch 240 may also be used to set the MMD into record mode, where a physical therapist, instructor, or trainer record a motion for the user to perform.

Figure 3:
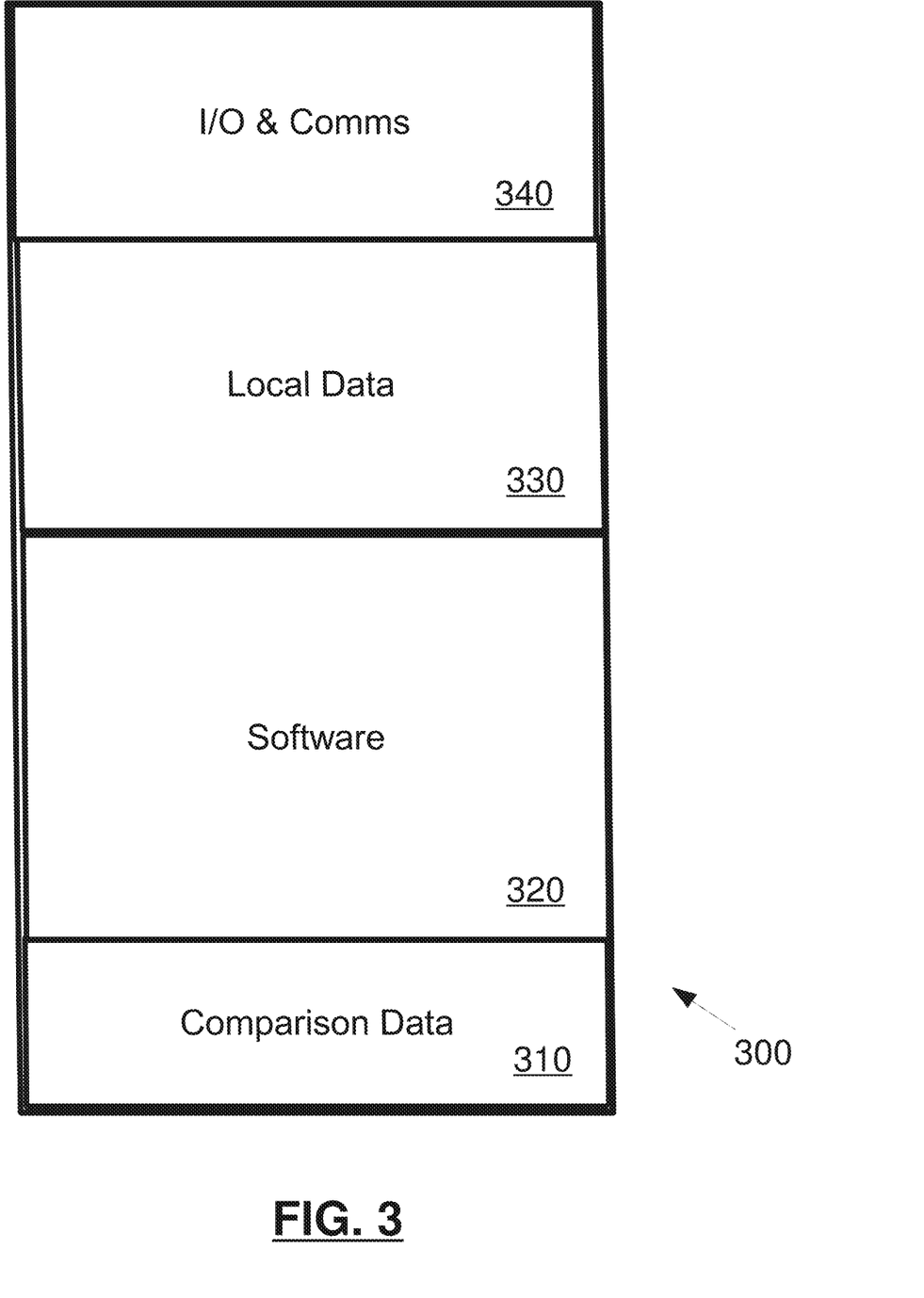
FIG. 3 is a diagram illustrating software and programming according to an embodiment of the present invention.

FIG. 3 is a diagram illustrating software and programming 300 according to an embodiment of the present invention. Comparison data 310 (e.g., stored, recorded, or downloaded motions/moves). The Comparison data may be recorded using the MMD 100 or another device. The comparison data may be downloaded from the Internet from a doctor, therapist, or sports enthusiast website.

Software 320 which may be, for example, downloaded software in executable form, firmware, or other electronics or programming types. The software 320 reviews IMU data and thereby compares a user's motions to a pre-recorded motion, and sets alarms as appropriate. The software 320 may optionally perform additional functions as described elsewhere herein.

Local data 330 may include, for example, buffered storage of IMU data, sections data, etc., and I/O & Comms 340 may include programming or data from any of data to or from the other components, and/or information protocols for wireless communications (e.g., Bluetooth) that may be utilized in other embodiments, expansion functionality, and retrieval of additional data or programming such as downloaded motions or moves, updates, etc.

FIG. 4 is a photograph of prototype electronics configured to implement an MMD 400 according to an embodiment of the present invention. As illustrated in FIG. 4, the invention may be implemented in an architecture including a motherboard 405 (e.g., Bluefruit feather board), IMU 404, power switch 403, piezo 402, and switch/selector 401. The MMD 400 illustrated is a prototype that implements the present invention by running software 320 on the motherboard and communicating with the IMU 404 and piezo 402.

Figure 5:
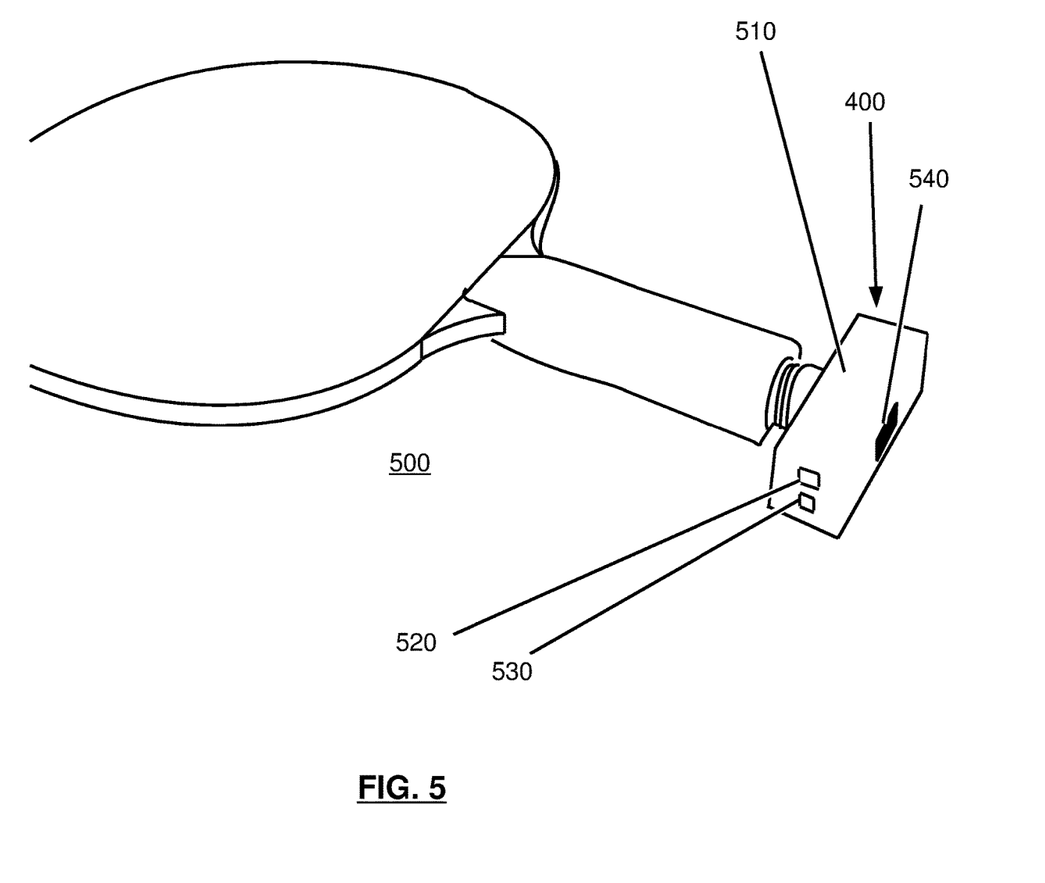
FIG. 5 is an illustration of a sports device having an attached MMD according to an embodiment of the present invention.

FIG. 5 is an illustration of a sports device 500 having an attached MMD 400 according to an embodiment of the present invention. Packaging 510 surrounds and encloses the protype MMD (MMD 400) such that the hardware is enclosed (so no electronics are sticking out). In one embodiment, it is desirable to have only a minimal amount of controls accessible on the MMD, which can be none (non-replaceable battery—or self-generating power supply, auto on/off, and Bluetooth downloadable motions, as one example). In the illustrated embodiment, only the power button and the flicker switch (e.g., switch/selector switch 401) are accessible and are placed so the user can interact with them. Preferably their functions are limited so the design is clean and easy to operate. Nonetheless, additional functionality may be added to the existing switches (e.g., pressing buttons twice to change programs, Multi-position selector switch, etc.) and included in other embodiments.

The packaging 510 is attached, for example, to sports equipment, and places the MMD at a location that allows the MMD to perform its functions by recording and/or comparing user movements for various strokes such as serves and returns in their numerous different forms.

User accessible power button 520, selector switch 530, and piezo (speaker) port 540 are also shown in FIG. 5. A power port for charging batteries (not shown) may also be included ([in various alternatives other power mechanisms may be utilized such as a solar panel (e.g., along a handle of a device), or an internal power generation mechanism such as one based on motion which can gain synergy from activities with significant amounts of motion.]).

Figure 6:
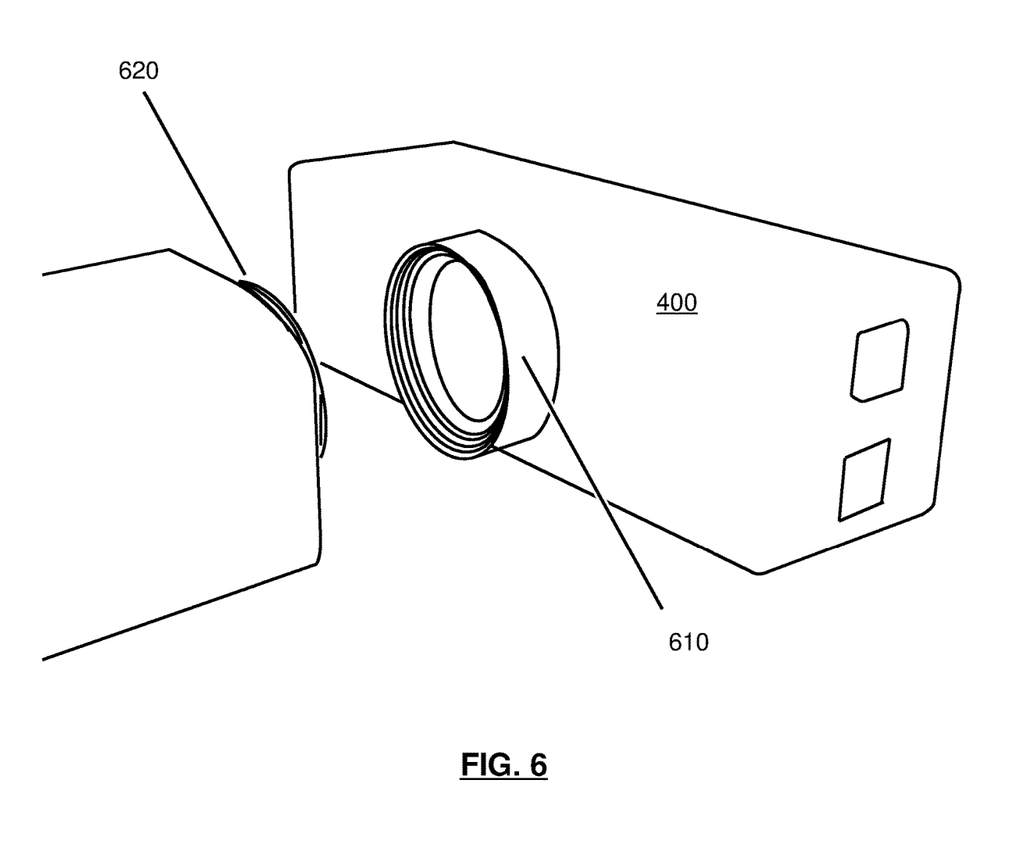
FIG. 6 is a drawing of an MMD attachment mechanism according to an embodiment of the present invention.

FIG. 6 is a drawing of an MMD attachment mechanism 600 according to an embodiment of the present invention. As illustrated the attachment mechanism comprises a threaded mount 620 attached to the sports device and a correspondingly threaded receiver 610 attached to packaging 510 of the MMD 400.

The mounting may be attached to any number of surfaces (or internal to a piece of equipment). The MMD itself may be attached any number of different mounts and mounting locations, including a small mount that goes underneath a table tennis paddle, a small mount that goes underneath a tennis racket, a wrist band to which the MMD can be attached (e.g., band 110 in FIG. 1 as one example).

The mount may include a shoe mount which is attached to the shoe (e.g., two bands on the side of the shoe). The MMD is then attached to the mount. The MMD may also be glue mounted onto a shoe or other equipment. Preferably, in a retail package for example, the MMD includes mounts for one or more surfaces, such as a flat surface, round surfaces, and mounts that can either be changed or adapt to different surfaces (e.g., flexible or cushioned mounts that conform to an irregular surface, for example. Each mount fitting to the MMD. Various other attachment mechanisms including adhesive, individual screw(s), latches, hook & loop (e.g., Velcro™), etc., may be utilized.

Figure 7:
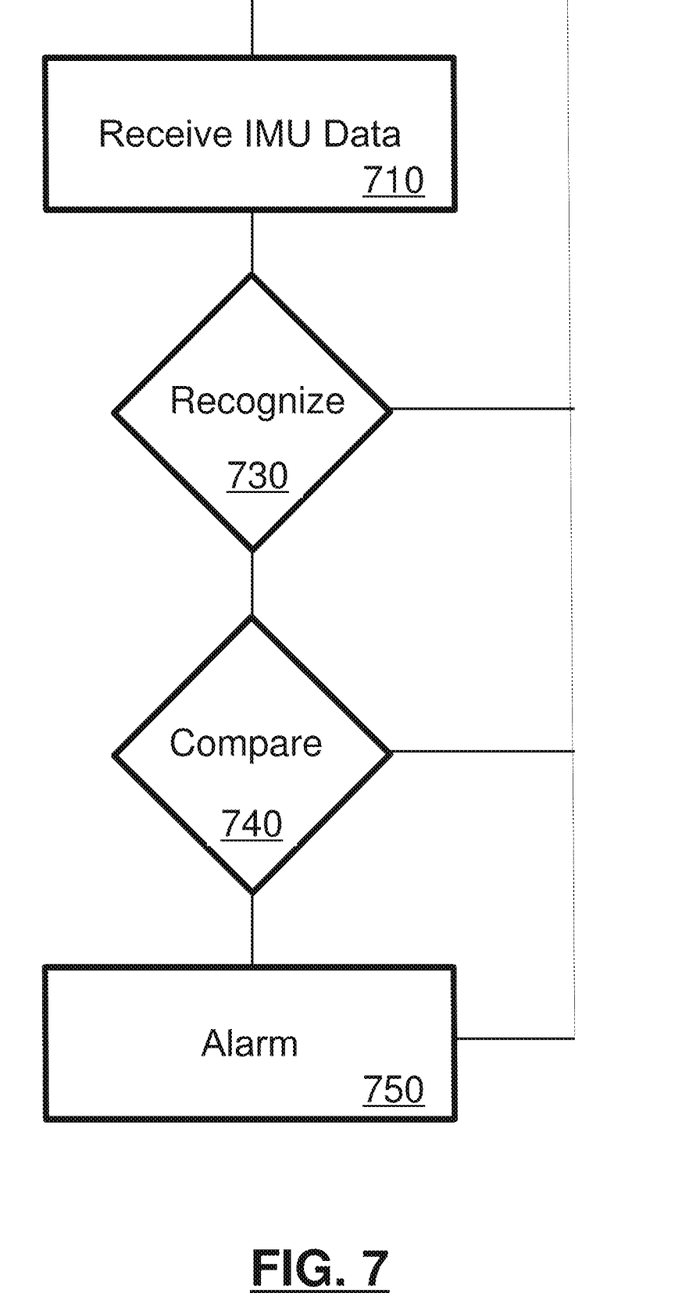
FIG. 7 is a flow chart of a motion comparison process according to an embodiment of the present invention.

FIG. 7 is a flow chart of a motion comparison process 700 according to an embodiment of the present invention. At step 710 IMU data is read. The IMU may be a multi-axis IMU, and may provide a position in 3D space, acceleration, and velocity. Other data may also be provided by the IMU depending on the board selected for implementing the MMD. Further additional features (and corresponding data) may be provided by add-on hardware or devices (e.g., such as altitude, lat/long, data from other equipment, other MMDs on a same user or another user, etc.).

In one embodiment, the present invention uses wireless communications to transact coordinated motions such as those between a quarterback and a receiver. In such embodiments, a 5G chip (not shown) may be fitted or connected to the motherboard to transmit instantaneous data to a remote server that coordinates timing, responses, in such synchronized activities and for individual activities as well.

Decision box 730 determines if the data being provided by the IMU is a selected or stored motion. The decision may need additional or previous cycles of IMU data which may be stored in local memory such as RAM. In one embodiment, a current motion is identified piece meal such that each cycle of IMU data is determined to be either consistent or inconsistent with a selected or stored move with respect to a number of previous IMU cycles (note consistent with a selected or stored motion is not necessarily the same as an acceptably correct motion (it may or may not be acceptable)). If the motion/move is not identified, the program loops back for the next IMU cycle.

Once enough IMU cycles have been received to identify the move, the compare is activated at step 740. Step 740 may be implemented in any manner that determines if the IMU data received matches or is within a predetermined tolerance of a stored move or motion. This may include, for example, a direct comparison of IMU sample values vs. a database of moves each having a similar set of samples. Each motion may be broken down into segments, such as natural segments of a swing (e.g., backswing, approach, impact, and follow-through), and specialized comparison routines invoked for each segment. In one embodiment, the saved or recorded motions are fitted to a curve and each corresponding IMU sample is compared to a corresponding location on the curve +/− a tolerance. Regardless of the method implemented, a pass or fail is determined for a current segment of the motion and, if failing, the alarm system is activated (step 750). If pass, the program loops back for the next IMU sample.

In one embodiment, a more detailed analysis of the collected IMU data is performed to determine how much or in what direction the user's motion is failing. If failing to one direction a certain tone or frequency of alarm is produced and, for example, either increasing or decreasing in volume or frequency to indicate whether the user's motion is getting worse or better.

In one embodiment, the MMD stores a plan for several different moves to be performed at different locations, such as a fitness track having stations. The location of the user at the fitness track triggers the MMD to evaluate the specific motion to be performed at that station (e.g., the users location selects the motion or a subset of saved motions for comparison).

As noted above, some embodiments of the invention include 5G communications, which can be arranged in many ways. In one embodiment 5G communication may be directly from the MMD to a remote server over a 5G network. All functions of the MMD and/or previously connected smartphone may be performed at the remote server and signaling for the application of haptics, alarms, etc. may be sent from the remote server to the MMD. Such embodiments can (but do not necessarily) eliminate the functions of the smartphone. Alternatively, the smartphone may be the hub that sends out the 5G communication (e.g., MMD communicates with smartphone which then forwards messages over the 5G network). The smartphone may still function as an interface with the MMD and interface with external databases and programs (e.g., APIs), displaying results, animations, statistics, etc. in user friendly formats.

Such communications in an ultra-low-latency 5G environment may form a tactile Internet experience. As discussed elsewhere herein, sounds of changing pitch can help guide the user to adjust motion toward the desired motion. Such guidance may be improved in a more fully tactile environment with things such as electrical stimuli (e.g., energizing electrodes on the MMD in contact with skin), spinning up of small physical gyros (e.g., an additional gyro pack inside the MMD, or a separate gyro pack/armband), and/or other devices that may also be energized in a way that guides, effects, or otherwise suggests, helps, or changes a user's motion toward the desired motion. Such other devices may include, for example, IoT devices attached to the user or near the user. The IoT devices may be publicly owned or accessible IoT devices. In one embodiment, additional sounds are provided to the user through remotely connected IoT speakers which are energized to provide moving or spatialized sound, such as Barco Auro, DTS:X, or other sound technologies such as Dolby Surround.

In one embodiment, the present invention is an MMD in an ultra-low-latency environment (e.g., 5G) forming a tactile Internet experience, wherein gryo readings from the MMD are transmitted via an ultra-low-latency network to a remote server for analysis comparing those readings to motions for identification and evaluation of the motion. The remote server configured to return signals identifying various analysis that may be, for example, a reward tone indicating a good motion, buzzers, sounds or other haptics identifying motions out of range of the desired motion—and such sounds/haptics may be arranged so as to help guide the user toward the desired motion. In one embodiment, the present invention comprises an MMD that only interacts with a remote server via a network, and a user's smart phone or other device (e.g., computer/website) communicate with the user to pass information from the user to the remote server and receive/display information about performance etc. from the remote server.

The communications to and from the MMD, remote server, smartphone, etc. may be compliant or compatible with one or more standards including, for example, 3GPP T522.261. Devices such as IoT, services, User Equipment (UE), and others in communication with the MMD, the remote server, or smartphone may similarly be compatible. Such devices may include IoT, Virtual Reality (VR), control, ubiquitous on-demand coverage, and such devices or variations thereof may be flexible to meet customized data gathering or feedback needs. Such devices include drivers that work within 3GPP or other standards including motion, video, navigation, and sound. In various embodiments, the focus being to use the 5G system in real-time (or near real-time) to support use of the MMD via a scalable and customizable network, with appropriate Key Performance Indicators (KPIs) (e.g., latency, reliability, data rates, etc.) at levels that enhance the user experience.

The present invention includes maintaining data as to user motions and classifying different users into group or levels of compliance with various motions (e.g., ranking tennis players based on how closely their backhands match typical professional backhand motions, ranking players of any sport based on consistency of matching professional players in any one or more specific or categories of motions). The present invention also includes maintaining data about user reactions to various alarms, haptics, or other feedback provided to users and the overall performance improvement of each user in relation to the types of feedback received. The present invention includes updating training regime and/or feedback according to results among all users through the identification of feedback regime that are more effective, and those that are more effective for a particular user.

Figure 8:
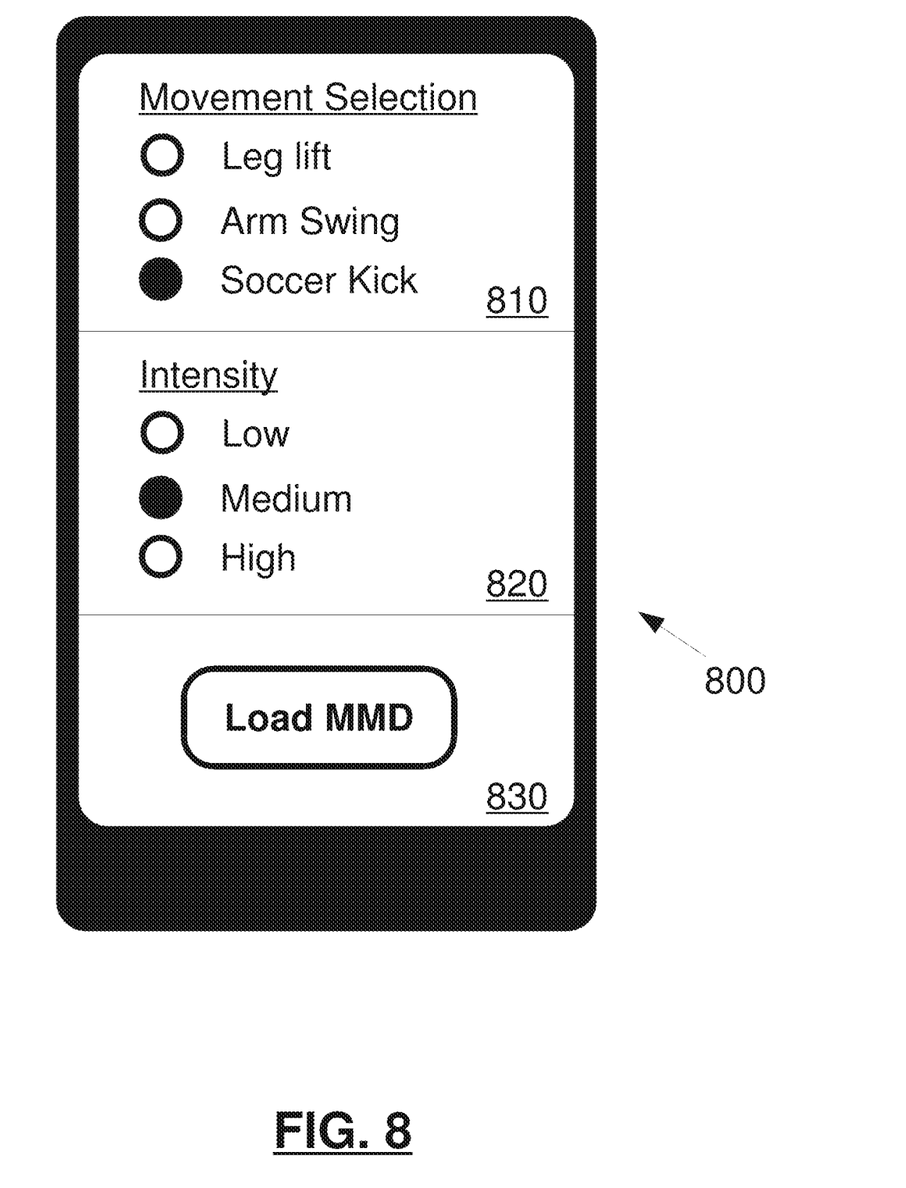
FIG. 8 is a screen shot of an application according to an embodiment of the present invention.

FIG. 8 is a screen shot of an application 800 according to an embodiment of the present invention. Radio buttons 810 are programmed for movement selection, here illustrating a lift, a swing, and a kick. The selections may include any number of other options including programs such as the fitness track program discussed above, a circuit of a gym, recorded moves (which may include options to customize the name), downloaded moves, etc. The programs may include variations of a program, such as program 1, variation A, B, and C, giving the user the same routine with slightly different motions so as to avoid repetitive motion injuries and to maintain additional flexibility.

Radio buttons 820 provide an additional variation as to intensity. Other features may be selected via radio buttons or other user interface types.

The MMD may applied to various activities, including, for example, automatic sports tracking at a gym for form at various weight stations, logging workout(s), and double as a wristband that merely id's the individual, and the IMU and other electronics may be automatically programmed to that a user's preferred settings when they are at a workout station. The MMD may also be programmed to provide include alerts to a trainer, gym manager, or others if things look bad (e.g., a move does not go as planned, or detects difficult situations, fals, etc.), like dropped weights.

One aspect of the present invention includes recognizing initial patterns of user movement indicative of the stroke to be performed, comparing the performed stroke in real-time or near real time to one or more stored strokes. Such intial patterns may be determined from analysis of the user's data and/or a large data set collected across multiple users (e.g., big data analysis). The present invention includes creating a stroke envelope composed of the limits of several different performances of a same stroke (by a same individual or by a plurality of any of trainers, professionals, groups, therapists, ranges of a big data analysis, etc.), and comparing a user's stroke to the stroke envelope. Such analysis may include dividing each motion into a plurality of segments and applyign an envelope to each segment.

In one embodiment, movements of trainers. professionals etc. are fit to a curve to which accelerometer and position data is applied. Accelerometer reading more than a certain degree, percentage, and or predetermined amount from the curve triggers the alert/alarm. The alarm volume may vary based on an amount outside the curve. For example, intensify for (larger amounts) or be subdued (smaller amounts). In another example, the alarm may have a tone frequency or an on/off staccato frequency that varies based on the amount outside the curve. The alarm may include a distinctive cut-off/turn-off sound when it is silenced upon return (or within tolerance) of the curve. Such decisions and comparisons are made, for example, by the electronics of the MMD and transmitted to a smartphone or other device for storage, display, and/or further analysis. Accordingly, the present invention includes a varying alarm wherein the variations are indicative of a characteristic of the motion performed.

Although the present invention may be implemented in various ways as will be understood by the skilled artisan in light of the disclosure herein, the present inventor has found great efficiency with an architecture that provides motion analysis at the MMD and then communicates motion analysis and/or other data to a remote mechanism such as a computing device, smartphone, or other device for either further analysis or display (such as any one or more of data, statistics, and/or simulations).

Motions may be detected in various ways. For example, Table 1 provides exemplary test code for determining a backhand when the MMD is used as a table tennis coach:

TABLE 1

| | |
|---|---|
| if ((imu.calcGyro(imu.gz)) > 1)<br>    delay (200);<br>    imu.readGyro( ); | {used to be 1 |
| if ((imu.calcGyro(imu.gx)) < −5 )<br>    delay (200);<br>    imu.readGyro( ); | { // used to be −3 |
|     if ((imu.calcGyro(imu.gz)) >3)<br>        delay (200);<br>        Serial.println("BACKHAND");<br>        imu.readGyro( );<br>        //testbackhand<br>    }<br>} | { // used to be 3 |

Table 1 illustrates a test case for a user performing a predetermined backhand. The table illustrates a test case where the user initiates a move and the values from the accelerometer (accelerometers) are tested to see if a successful backhand has been performed. As shown in Table 1, values from the gyroscope (or multiple gyroscopes, different gyroscopes set on different axes, for example) are tested to see if they correlate with predetermined values of a backhand.

In one embodiment, multiple gyroscope values are similarly tested in simultaneous or near simultaneous real-time and evaluated against a plurality of moves which may include backhand, forehand, and any number of variations of those moves (e.g., upper-cut backhand topspin, down-cut backhand backspin, x-cut backhand off-table spin, cross-court backhand flat, as a small set of possible moves evaluations). In one embodiment, the evaluations can share comparison values to the extent practical or they may be implemented with separate comparison values for each instance of a move. For each instance of move, stored values may include a range of acceptable values as maximum or minimums, percentages etc.

In one embodiment a percentage is implemented and the percentage varies from one instance to the next such that, for example, in portions of a move where higher accuracy or precision is either necessary or desired lower percentage variance is provided for corresponding instances in the comparison. For example, follow though may have more variance than instances before contact.

In one embodiment, the variances decrease (lower percentage tolerance) with each instance prior to contact and decrease rapidly after contact, such the variances may, for example, continually change but change more rapidly at key points such as just prior and just after contact. The variances (or tolerances) may change from value to value or they may be assigned for a segment, and segments may vary in length or amount/number of data points in each segment.

In this example, the delay (200) is a designated delay in milliseconds between recording/testing values (which is performed 5 times per second) during a specific move. Since table 1 is a test, testing/checking was not necessary at a great speed, which is easily modified to test many times per second such that a continuum of values replicating the move without any one value being significantly higher or lower than its neighboring values even though the direction and/or acceleration through the move changes rapidly when a user observes a move being executed. Such testing may be performed at 300 or more times per second.

An additional example is provided in Table 2.

TABLE 2

```
if                              ((imu.calcGyro(imu.gz))      >    2){
        delay(200);
        imu.readGyro( );
            if                  ((imu.calcGyro(imu.gx)) > −5 ) {   // forehand test
starts                                                                            here
                delay(200);
                imu.readGyro( );
                    if          ((imu.calcGyro(imu.gy))      <    3) {
                        delay(200);
                        ble.print("AT+BLEUARTTX=");
//                                                                       ble.readline( );
        ble.println(forehandstat);
        ble.print("AT+BLEUARTTX=");
//                                                                       ble.readline( );
        ble.println("        :                                              FOREHAND");
                        //Serial.println("FOREHAND");
                        forehandstat++;
                        //Serial.println(forehandstat);
                        //waiting( );
                        delay(1000);
                        imu.readGyro( );
                    }
                }
            else{               // if it was not backhand, 'else' test for
backhand
                    if          ((imu.calcGyro(imu.gx))      <   −5  ) {
                        delay(200);
                        imu.readGyro( );
                        if      ((imu.calcGyro(imu.gy))      >    3) {
                        delay(200);
                        //Serial.println("BACKHAND");
                        ble.print("AT+BLEUARTTX=");
                        //ble.readline( ) ;
                        ble.println("                                        BACKHAND:n");
                        //ble.readline( );
                        ble.print("AT+BLEUARTTX=");
                        //ble.readline( );
                        ble.println{"-----");
                        ble.print("AT+BLEUARTTX=");
                        //ble.readline( );
                        ble.println{backhandstat);
                        backhandstat++;
                        //Serial.println{backhandstat);
                        //waiting( );
                        delay(1000);
                        imu.readGyro( );
                    }
                }
            }
        }
}
```

As shown in Table 2, the routine tests first for forehand and then for backhand. The forehand test reads the IMU data for one or more axes. Here, for example, the x-axis of the IMU is read first and tested for a value that indicates a right to left forward swing (e.g., >−5). If the value read is what is expected of a forehand in that axis, then another axis is tested, in this example, the y-axis where a <−3 value (in combination with appropriate x-axis value) affirmatively identifies a forehand.

The present invention includes testing multiple axes for first indications of a particular stroke. The multiple axes may be the x and y axes as provided in Table 2, or it may be a series of different x, y, and/or z axes set in different spatial orientations. The initial motions (and the full motions to evaluate the entire stroke against) for each stroke is preferably provided by the user, coach, or downloaded as discussed herein. The initial motions may be extracted from practice motions by the user or coach. In one embodiment the present invention utilizes a limited number of axes to recognize a motion and then processes a larger number (a plurality) of differently oriented axes to evaluate that particular motion.

If the forehand test fails, the program drops down to test for backhand. The values tested may include the same values previously read from the IMU(s) or they may be freshly read. In at least one embodiment some of the IMU values are shared between tests and some IMU readings are new.

The example in Table 2 is an initial test for particular strokes (forehand, and backhand). The test may be extended to the various other strokes and to sub-categories of strokes (e.g., forehand with top-spin, forehand with backspin, etc.). In one embodiment, the if then else structure is extended for any number of motions. In another embodiment, a programmable test loop repeats and reads in a different set of parameters identifying each of different motions which are tested individually and moving on to the next if the test is not passed. In one embodiment, the first test is the most used motion, thereby eliminating unnecessary tests if the most used motion is tested first. In one embodiment, the MMD tracks motions practiced or used by a user and readjusts programming such that the most common motions are tested first.

Further additional routines are implemented to evaluate the particular stroke and provide feedback in real time as the stroke is practiced. The delay time illustrated (200) is for test purposes and a functional device would test at a much faster pace (e.g., 5 ms, 1 ms, or less depending on hardware capabilities). Such additional routines may be programmed in a similar architecture such IMU values are read at, for example, predetermined intervals and/or at portions of a motion which are compared to a range of expected values for that motion at that time and which are, for example, provided from a recorded practice move, downloaded, etc.

It should be noted that the ble.println commands implement Bluetooth communication between the MMD and a computing device such as a smartphone app. Here, the command identifies the motion (stroke) as either forehand or backhand. However, in an operation device, such a command may be utilized to signal auditory or vibrations feedback for example. The results will also be sent to a smartphone (or other computing device) which can then utilize the results to implement any of the features discussed herein and may include the ability to review moves including simulated motion, highlighting desirable corrections, etc. The smartphone may also communicate the data for further analysis or storage retrievable by others for yet further comparison, analysis or improvement in either.

The examples provide for communication between the MMD and smartphone as necessary or desired for various smartphone (or other external computing device) features. And all data, which may include raw, MMD pre-processed, MMD processed data, or a combination thereof may be transmitted to enable various external features (such as a smartphone display).

In one embodiment, the MMD does not utilize a smartphone at all and the user interface is clean. The MMD is, for example, programmed to recognize a set of moves, each of which is evaluated and feedback provided to the user directly from the MMD. The feedback is, for example, when a larger than expected value for the identified motion occurs (e.g., too fast) a high pitched or high frequency beep occurs, and, if too slow, a lower pitch or lower frequency beep is sent. The feedback may be implements in an if/then/else programming structure.

In addition to the MMD, the present invention includes collection, consolidation, and analysis of data from disparate devices connected over a 5G network. Such data may include video from cameras positioned to observe practice, play, therapy, or other uses of the MMD. Such data may be collected via cell phone cameras of bystanders, therapists, and others, security cameras. Such data is not limited to video and may include audio, social media posts, data from IoT devices, etc. In some cases, the speed of collection and transmission is sufficient to provide near-real time additions to motion or other analysis performed. Such data may be provided to enhance application experience such as for example, a replay of a motion where the user watches the replay on an app or computer monitor that may include actual video and feedback similar to that provided while performing the motion.

Such replays would typically be performed on a smartphone or computer and include a split screen playback where one side is a video of the overall move (e.g., user's upper body, or entire body) and the other side providing a closeup of the body part whose motion most influences the quality of the move (e.g., hand or wrist). The MMD may also be shown in the videos, and may, for example, light-up, highlight, or other indicia at times when the MMD was buzzing during the move. In one embodiment, the MMD also buzzes on the user's wrist during playback so the user can be more aware of the critical points in the move being reviewed and the motion to be corrected.

The present invention includes use of IoT data from different devices, and that data may be amalgamated into databases or other storage in the cloud or at the user's smartphone, computer, etc. Such data may be processed, correlated, and cross-correlated and fed into an API to find patterns or situations that effect a user's workout, therapy, or other activity in either positive or negative ways. Such data is useful to the user in planning for events or other activities where the motion is to be used.

Although the present invention has been described herein with reference to a motherboard IMU circuit board implementation, the devices and processes of the present invention may be applied to other devices including existing platforms having sufficient motion detection and processing power, such as for example, a smart phone may be configured as an MMD, an Apple watch may be configured as an MMD, if running an appropriate program (e.g., application) to capture and analyze motions according to the teachings of the present invention. Further the MMD may take the form of a smartwatch or other device.

In one embodiment, MMDs are utilized on different pieces of equipment, such as on a wrist band and/or on a shoe. The audio prompts may be transmitted to a speaker or an earpiece (e.g., a wireless Invisible In Canal (IIC) device) to guide and/or provide feedback to the user. Collected data may be transmitted to the user's smartphone and the disparate data streams combined in side-by-side or over/under (charts or statistics, for example, e.g., number/percentage of correct moves, degree of variation, average amount outside envelope, etc.).

In one embodiment, MMDs are utilized in conjunction with each member of a team, a subset of a team, and/or members on opposing teams. For example, MMDs installed on shoes of soccer players. Each MMD communicating with a central collection point in communication with a smart phone or other computing device. The collection may be performed by, for example, a network of receivers at different locations on a sideline(s) of a playing field, receivers placed on goalposts, mobile devices on field (e.g., clipped to a referee's belt). The data can be analyzed and provided in graphic form to a coach for evaluation. The data may be displayed to show or identify coordination between the players and providing data for coaching evaluation. Such data may be provided in tandem with video showing the moves corresponding to the data.

In describing preferred embodiments of the present invention illustrated in the drawings, specific terminology is employed for the sake of clarity. However, the present invention is not intended to be limited to the specific terminology so selected, and it is to be understood that each specific element includes all technical equivalents which operate in a similar manner. For example, when describing an accelerometer, compass, or other components, any equivalent or other device having a similar function or capability, whether or not listed herein, may be substituted therewith. Furthermore, the inventor recognizes that newly developed technologies not now known may also be substituted for the described parts and still not depart from the scope of the present invention. All other described items, including, but not limited to smartphones, motherboards, sports equipment, attachment mechanisms, training routines, moves, etc., should also be considered in light of any and all available equivalents.

The present invention includes a device comprising an accelerometer, a processing device configured to receive data from the accelerometer and compare motion(s) indicated by the accelerometer data to previously stored motion(s), and a feedback mechanism configured to notify a user of the device about at least one aspect of a user motion. The device may further comprising a wireless link between the accelerometer and processing device for communicating data from the accelerometer and feedback signals to the feedback mechanism.

The accelerometer and feedback mechanism may be mounted on a wrist/ankle attachable band, and/or the accelerometer may attached to a sports equipment item. The accelerometer may be embedded in a smart watch.

The feedback mechanism may comprise multiple points of feedback individually energized in a manner representative of motion error identified in the accelerometer data. The feedback may be different for different variations of a desired motion.

The device may calculate at least one aspect of a user motion comprising an amount of deviation from a desired motion. The variation may be communicated to the user via at least one of volume and frequency of the feedback. The amount of variation may comprise an amount of variation in at least one of position at a predetermined portion of the motion and speed at the predetermined portion of the motion. The reference motion may, for example, comprise at least one of a motion recorded by the device via a user motion, a motion recorded by a similar device by a coach or trainer, and a motion pre-recorded and downloaded to the device.

The present invention may be embodied as a method of analyzing motion data, comprising the steps of receiving accelerometer data, identifying a relevant motion in the accelerometer data, comparing the relevant motion to a reference motion, and sending feedback indicative of the comparison. The step of comparing may comprise comparing at least one of up/down (e.g., x axis), left/right (e.g., y axis), and forward/backward (e.g., z axis) motions to the reference motion. (the axes may be labeled differently). The step of comparing may comprise feeding the accelerometer data into an equation representative of the reference motion. The equation may include a margin of acceptable motion error which identifies whether negative feedback signals are to be issued.

The step of comparing comprises comparing data points of accelerometer data to corresponding synched accelerometer datapoints accelerometer of the reference motion. The feedback may comprise an audible or vibrational notification indicative of an incorrect motion. The feedback may comprise a higher pitch audible alarm when the motion is generally too high and a lower pitch when the motion is too low.

The method may further comprise the step of communication with a remote device operated by a professional and receiving or downloading prescribed or suggested moves from the remote device. And, the method may further comprise a step of recording accelerometer data during a demonstration motion and using the recorded accelerometer data to determine if a subsequent motion is similar within a predetermined envelope.

Portions of the present invention may be conveniently implemented using a conventional general purpose or a specialized digital computer or microprocessor programmed according to the teachings of the present disclosure, as will be apparent to those skilled in the computer art.

Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art based on the present disclosure.

The present invention includes a computer program product which is a storage medium (media) having instructions stored thereon/in which can be used to control, or cause, a computer to perform any of the processes of the present invention. The storage medium can include, but is not limited to, any type of disk including floppy disks, mini disks (MD's), optical discs, DVD, HD-DVD, Blue-ray, CD-ROMS, CD or DVD RW+/−, micro-drive, and magneto-optical disks, ROMs, RAMs, EPROMs, EEPROMs, DRAMs, VRAMs, flash memory devices (including flash cards, memory sticks), magnetic or optical cards, SIM cards, MEMS, nanosystems (including molecular memory ICs), RAID devices, remote data storage/archive/warehousing, or any type of media or device suitable for storing instructions and/or data.

Stored on any one of the computer readable medium (media), the present invention includes software for controlling both the hardware of the general purpose/specialized computer or microprocessor, and for enabling the computer or microprocessor to interact with a human user or other mechanism utilizing the results of the present invention. Such software may include, but is not limited to, device drivers, operating systems, and user applications. Ultimately, such computer readable media further includes software for performing the present invention, as described above.

Included in the programming (software) of the general/specialized computer or microprocessor are software modules for implementing the teachings of the present invention, including, but not limited to, recording motion data, analyzing motion data, comparing motion data, outputting alerts/alarms/sounds, including voices, and the display, storage, or communication of results according to the processes of the present invention.

The present invention may suitably comprise, consist of, or consist essentially of, any of element, part, or feature of the invention and their equivalents as described herein. Further, the present invention illustratively disclosed herein may be practiced in the absence of any element, whether or not specifically disclosed herein. Obviously, numerous modifications and variations of the present invention are possible in light of the above teachings. It is therefore to be understood that within the scope of any claims, the invention may be practiced otherwise than as specifically described herein.

What is claimed is:

1. A device comprising:
   an accelerometer;
   a processing device configured to receive accelerometer data from the accelerometer, identify a relevant motion in the accelerometer data, and compare the motion to previously stored motion(s); and
   a feedback mechanism configured to notify a user of the device about at least one aspect of the motion derived from the comparison while the motion is occurring;
   wherein:
   the feedback mechanism comprises multiple points of feedback individually energized in a manner representative of a magnitude of motion error identified in the accelerometer data;
   the feedback is a different pitch or tone for different variations from a desired motion;
   the at least one aspect of a user motion comprises an amount of deviation from a desired motion; and
   the notification of the at least one aspect occurs while the deviation is occurring.

2. The device according to claim 1, wherein the amount of variation is communicated to the user via at least one of volume and frequency of the feedback.

3. The device according to claim 1, wherein the amount of deviation comprises deviation in at least one of position at a predetermined portion of the motion and speed at the predetermined portion of the motion.

4. The device according to claim 1, wherein the previously stored motion(s) comprises at least one of a motion recorded by the device via a user motion, a motion recorded by a similar device by a coach or trainer, and a motion pre-recorded and downloaded to the device.

5. The device according to claim 1, wherein an identified motion is compared to a plurality of stored motions and wherein the comparisons are performed in order starting with a most common motion first.

6. The device according to claim 1, wherein the motions are identified via multiple axis testing.

7. The device according to claim 1, wherein the comparison comprises dividing each motion into a plurality of segments and applying an envelope to each segment.

8. The device according to claim 1, further comprising recognizing initial patterns of user movement indicative of a stroke to be performed, comparing the stroke in real-time or near real time to a corresponding stored motion, wherein the initial patterns are determined from analysis of a large data set collected across multiple users.

9. The device according to claim 1, wherein the comparison data is determined based on a location of the user such that the comparison is selected based on a motion appropriate to the location.

10. The device according to claim 1, wherein the comparison is performed by dividing the motion into segments and applying a specialized comparison for a segment.

11. The device according to claim 10, wherein the specialized comparison comprises a set of data fitted to a curve and applying the motion to the curve.

12. The device according to claim 1, wherein the notification to the user is a non-alpha numeric audio or vibrational notification that is corrective in degrees such that it indicates an amount and direction of corrective action needed by the user to transform the motion in to a desired motion.

* * * * *